United States Patent
Li et al.

(10) Patent No.: US 12,226,083 B2
(45) Date of Patent: Feb. 18, 2025

(54) HOLDER AND SURGICAL INSTRUMENT ASSEMBLY FOR INTERVERTEBRAL FORAMEN ENDOSCOPE FUSION

(71) Applicant: BEIJING FULE SCIENCE & TECHNOLOGY DEVELOPMENT CO., LTD., Beijing (CN)

(72) Inventors: Zhenzhou Li, Beijing (CN); Guoping Fan, Beijing (CN); Xiyi Huang, Beijing (CN); Yuanzhi Xu, Beijing (CN); Yaling Wang, Beijing (CN)

(73) Assignee: BEIJING FULE SCIENCE & TECHNOLOGY DEVELOPMENT CO., LTD, Beijing (CN)

( * ) Notice: Subject to any disclaimer, the term of this patent is extended or adjusted under 35 U.S.C. 154(b) by 911 days.

(21) Appl. No.: 17/417,600

(22) PCT Filed: Mar. 25, 2020

(86) PCT No.: PCT/CN2020/081038
§ 371 (c)(1),
(2) Date: Jun. 23, 2021

(87) PCT Pub. No.: WO2021/184402
PCT Pub. Date: Sep. 23, 2021

(65) Prior Publication Data
US 2022/0330809 A1    Oct. 20, 2022

(30) Foreign Application Priority Data

Mar. 18, 2020    (CN) .......................... 202010190792.9
Mar. 18, 2020    (CN) .......................... 202020341444.2

(51) Int. Cl.
*A61F 2/46*    (2006.01)
*A61B 1/317*    (2006.01)
*A61F 2/44*    (2006.01)

(52) U.S. Cl.
CPC ............ *A61B 1/317* (2013.01); *A61F 2/4455* (2013.01); *A61F 2/4611* (2013.01); *A61F 2002/4627* (2013.01); *A61F 2002/4629* (2013.01)

(58) Field of Classification Search
CPC ............................. A61F 2/4455; A61F 2/4611
See application file for complete search history.

(56) References Cited

U.S. PATENT DOCUMENTS

| 2014/0188226 A1 | 7/2014 | Neary et al. |
| 2018/0110629 A1* | 4/2018 | Ewer ............... A61F 2/4455 |

(Continued)

FOREIGN PATENT DOCUMENTS

| CN | 101268963 A | 9/2008 |
| CN | 201147351 Y | 11/2008 |

(Continued)

OTHER PUBLICATIONS

International Search Report, PCT/CN2020/081038, May 5, 2021, 10 pages (Chinese language only).

(Continued)

*Primary Examiner* — Si Ming Ku
(74) *Attorney, Agent, or Firm* — Faegre Drinker Biddle & Reath LLP

(57) ABSTRACT

A holder for intervertebral foramen endoscope fusion includes an inner rod, an anti-torsion sleeve and an outer sleeve which are sleeved from inside to outside and are movable relatively along an axial direction. The inner rod is configured for pushing the expanding part inside a fusion cage. A head end of the anti-torsion sleeve is provided with an external thread section, the external thread section is configured for matching and connecting with the screw plug mounting hole of a holding body of the fusion cage, and the tail end of the anti-torsion sleeve is provided with a match- (Continued)

ing structure for matching with the bone grafting funnel. A head end of the outer sleeve is matched with the holding body of the fusion cage to restrict the rotation of the fusion cage along an axis of the fusion cage. A surgical instrument assembly is also provided.

9 Claims, 15 Drawing Sheets

(56) References Cited

U.S. PATENT DOCUMENTS

2019/0224024 A1 7/2019 Kleiner et al.
2022/0330809 A1 10/2022 Li et al.

FOREIGN PATENT DOCUMENTS

| CN | 100584283 C | * | 1/2010 |
| CN | 203436365 U | | 2/2014 |
| CN | 207928360 U | | 10/2018 |
| CN | 1019124834 A | | 1/2019 |
| CN | 110114040 A | | 8/2019 |
| CN | 110584844 A | | 12/2019 |
| CN | 212592583 U | | 2/2021 |
| EP | 3357459 A1 | | 8/2018 |
| WO | 2021184402 A1 | | 9/2021 |

OTHER PUBLICATIONS

The State Intellectual Property Office of People's Republic of China; Chinese Application No. 202010190792.9; First Office Action; 27 pages; dated Aug. 28, 2024.

* cited by examiner

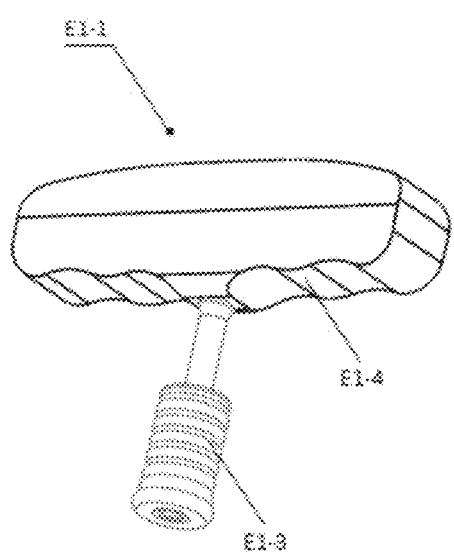
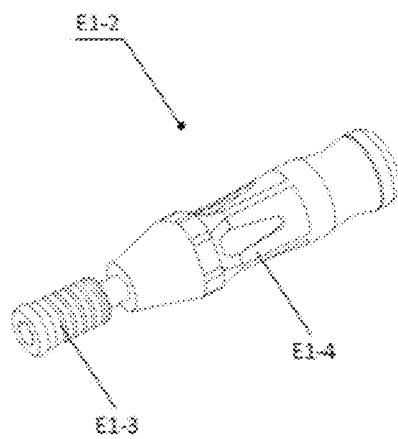
Figure 10-1  Figure 10-2

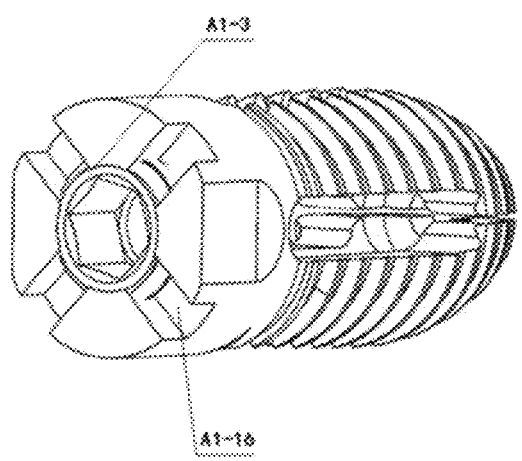 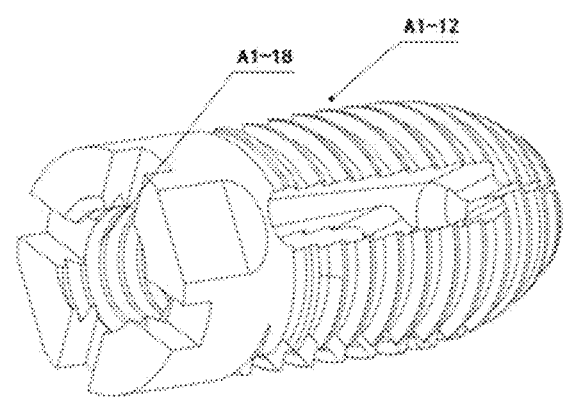
Figure 13-1                    Figure 13-2

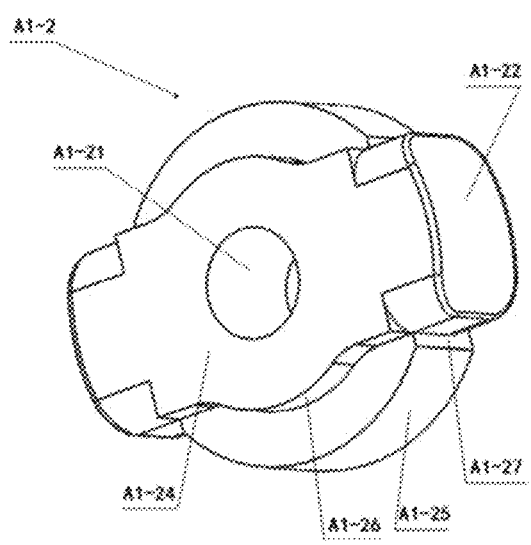 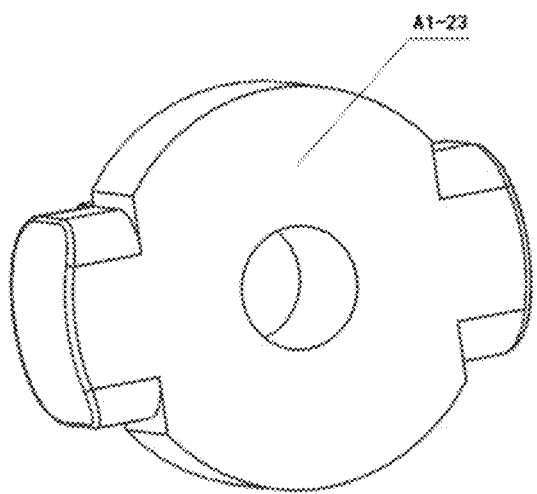
Figure 14-1    Figure 14-2

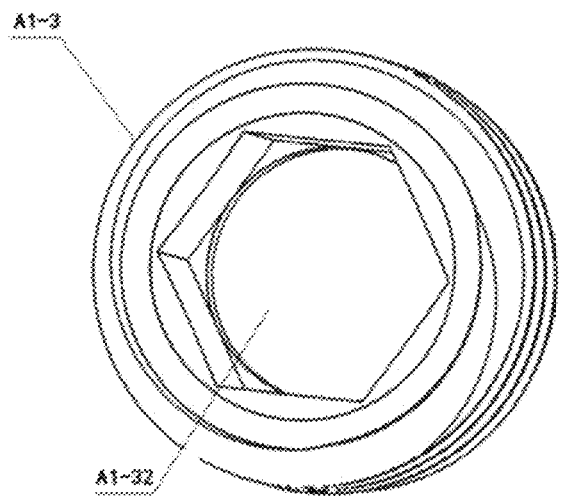 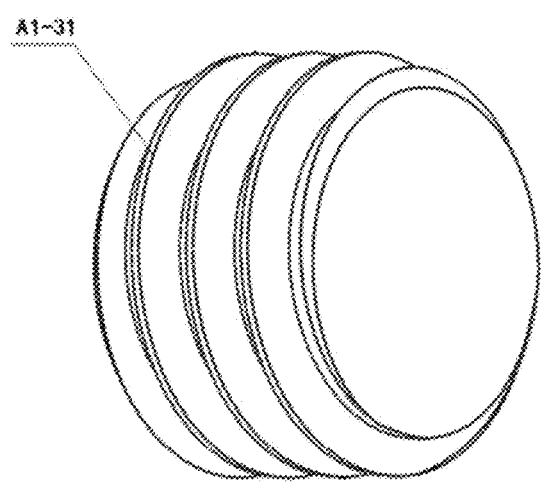
Figure 15-1  Figure 15-2

HOLDER AND SURGICAL INSTRUMENT ASSEMBLY FOR INTERVERTEBRAL FORAMEN ENDOSCOPE FUSION

The present application is a national stage application of PCT application No. PCT/CN2020/081038, which claims the benefit of priorities to the following two Chinese patent applications, all of which are incorporated herein by reference in their entireties,
1) Chinese Patent Application No. 202010190792.9, titled "HOLDER AND SURGICAL INSTRUMENT ASSEMBLY FOR INTERVERTEBRAL FORAMEN ENDOSCOPE FUSION", filed with the China National Intellectual Property Administration on Mar. 18, 2020, and
2) Chinese Patent Application No. 202020341444.2, titled "HOLDER AND SURGICAL INSTRUMENT ASSEMBLY FOR INTERVERTEBRAL FORAMEN ENDOSCOPE FUSION", filed with the China National Intellectual Property Administration on Mar. 18, 2020.

FIELD

The present application relates to the technical field of medical apparatus, and in particular to a holder and surgical instrument assembly for intervertebral foramen endoscope fusion.

BACKGROUND

Intervertebral fusion using the safety triangle approach through the intervertebral foramina is currently known as an intervertebral surgery method with high surgical safety. The fusion is performed under the endoscope through the intervertebral foramen endoscope. The surgical incision is only a few millimeters, and the traumatic surface is very small. The muscle, soft tissue, nerve and ligamentum flavum of the patient are avoided from suffering trauma during the operation, and the spinal diseases such as degenerative lumbar spondylotisthesis, lumbar disc herniation and unstable/narrowing of intervertebral space may be solved without causing secondary injury to the patient. The operation is performed under the patient's local anesthesia, and the condition of the lesion may be clearly observed through the intervertebral foramen endoscope. The visual operation brings high sally and maneuverability.

The fusion is operated through an implant (fusion cage), highly matched, practical and efficient surgical instruments, and an intervertebral foramen endoscope. At present, the inflatable fusion cage matches the physiological shape of the lumbar intervertebral disc (that is, the anterior disc thickness is greater than the posterior disc thickness). Most of the surgical instruments that may be used for inflatable fusion cages on the market have few functions, and most of them can not function as others except holding the fusion cage alone or open the fusion cage. If bone grafting is needed for the fusion cage, a further instrument, i.e., a bone grafting funnel, should be used to match the fusion cage. In practice, the surgical steps such as implantation, distraction, bone grafting and cap sealing of intervertebral fusion cage involve more instruments. These instruments pass through the working channel of the operation for many times. This increases the workload of doctors, also, the frequent collision and wear of the working channel and the device may also shorten the life of the instrument and the channel.

In addition, the "ultra-minimally invasive surgery" under endoscope must be equipped with an intervertebral foramen endoscope, and the incision of several millimeters determines that each intervertebral treatment instrument matched with the intervertebral foramen endoscope must be matched with the small-diameter working channel of the intervertebral foramen endoscope. Traditional intervertebral treatment instruments are composed of a long pole, a handle, and an operating head (different in form and function according to surgical requirements). The instrument extends from the tail end of the intervertebral foramen endoscope to the focus of intervertebral space, and its operating head is smaller than the diameter of the working channel of the intervertebral foramen endoscope. Actually, the small operating head operates a small acting area.

For a patient with a history of intervertebral disc disease or a more serious condition, there are more intervertebral discs that need to removed. Therefore, the instrument with a small operating head must be inserted into the large-area diseased intervertebral disc through the intervertebral foramen endoscope for multiple treatments. Statistics data shows that, the doctor usually takes more than minutes to merely take out the intervertebral disc for such complicated patient. A single operation for a long time not only makes the doctor tired at work, and too long anesthesia may also have a negative impact on the patient.

Therefore, how to provide an efficient and high-quality endoscopic intervertebral foramen fusion is expected by those skilled in the art.

SUMMARY

The present application provides a hokier for intervertebral foramen endoscope fusion, comprising an inner rod, an anti-torsion sleeve and an outer sleeve which are sleeved from inside to outside and are movable relatively along an axial direction; wherein
the inner rod is configured for pushing the expanding part inside a fusion cage;
a head end of the anti-torsion sleeve is provided with an external thread section, the external thread section is configured for matching and connecting with the screw plug mounting hole of a holding body of the fusion cage, and the tail end of the anti-torsion sleeve is provided with a matching structure for matching with the bone grafting funnel; and
a head end of the outer sleeve is matched with the holding body of the fusion cage to restrict the rotation of the fusion cage along an axis of the fusion cage.

During the operation, the anti-torsion sleeve and the outer sleeve of the holder are combined in vitro, and then the anti-torsion sleeve is threadedly connected with the screw plug mounting hole of the fusion cage, and the outer sleeve and the holder are circumferentially limited and matched to realize the clamping of the fusion cage; then an assembly formed by the combined holder and the fusion cage is sent into the body, and then the inner rod is inserted into the anti-torsion sleeve, so that the head end of the inner rod pushes the expanding part to move to the head end position of the support body in an axial direction to increase the radial size of the support body and realize the expansion of the fusion cage. After the expanding part moves to the preset position, the inner rod may be taken out from the anti-torsion sleeve, and then the bone grafting funnel is mounted on the tail end matching structure of the anti-torsion sleeve for bone grafting operation. After bone grafting is completed, the anti-torsion sleeve is screwed out of the fusion cage and taken out of the body, and the end of the pre-tightening wrench fixed with the screw plug extends from the inner cavity of the outer sleeve and is mounted in the screw plug mounting hole of the fusion cage to complete the cap sealing operation. Finally, the outer sleeve is separated from the fusion cage and taken out of the body.

It may be seen from the above description that the holder provided by the present application may realize the functions of holding, implanting, expanding, bone grafting, cap sealing, etc., which may greatly reduce the operation workload of doctors and realize efficient and high-quality operation.

In addition, the present application further provides a surgical instrument assembly for intervertebral foramen endoscope fusion, comprising:

the holder for intervertebral foramen endoscope fusion according to any one of the above; and a fusion cage and a bone grafting funnel, wherein the fusion cage comprises a fusion cage body and an expanding part, wherein the fusion cage body comprises a holding body and expanding bodies, the number of the expanding bodies is at least two, and the expanding bodies are circumferentially arranged along one end of the holding body;

wherein the expanding bodies encloses an inner cavity, and a bone overflow channel is formed between at least part of adjacent ones of the expanding bodies;

wherein the holding body is provided with a screw plug mounting hole communicated with the inner cavity, and the screw plug mounting hole is threadedly matched with an external thread section arranged at the head end of the anti-torsion sleeve;

wherein the expanding part is slidably arranged in the inner cavity, and a slideway is formed between two adjacent ones of part of the expanding bodies, the slideway extends in a longitudinal direction, and the closer to an head end of the spreading body, the narrower the slideway, and the expanding part has an expanding shoulder that is slidingly matched with the slideway; and wherein a clamping groove is provided at a head end of the inner cavity wall, and the expanding part is clamped in the clamping groove in the case that the expanding shoulder slides to the head end of the expanding body.

Since the surgical instrument assembly in this application includes any of the above-mentioned holders, the surgical instrument assembly also includes the above-mentioned technical effects of the holder.

BRIEF DESCRIPTION OF THE DRAWINGS

FIG. 10-1 is a structural schematic diagram of a vertical quick-release handle according to an embodiment of the present application;

FIG. 10-2 is a structural schematic diagram of a longitudinal quick-release handle according to an embodiment of the present application:

FIG. 13-1 is a structural schematic diagram of a fusion cage from the view of a rear side during assembling according to an embodiment of the present application;

FIG. 13-2 is a structural schematic diagram of a fusion cage from the view of a rear side during assembling according to an embodiment of the present application in another direction;

FIG. 14-1 is a structural schematic diagram of the front of an expanding part according to an embodiment of the present application;

FIG. 14-2 is a structural schematic diagram of the back of an expanding part according to an embodiment of the present application:

FIG. 15-1 is a structural schematic diagram of one side of a screw plug according to an embodiment of the present application;

FIG. 15-2 is a structural schematic diagram of the other side of a screw plug according to an embodiment of the present application;

Figure 1:
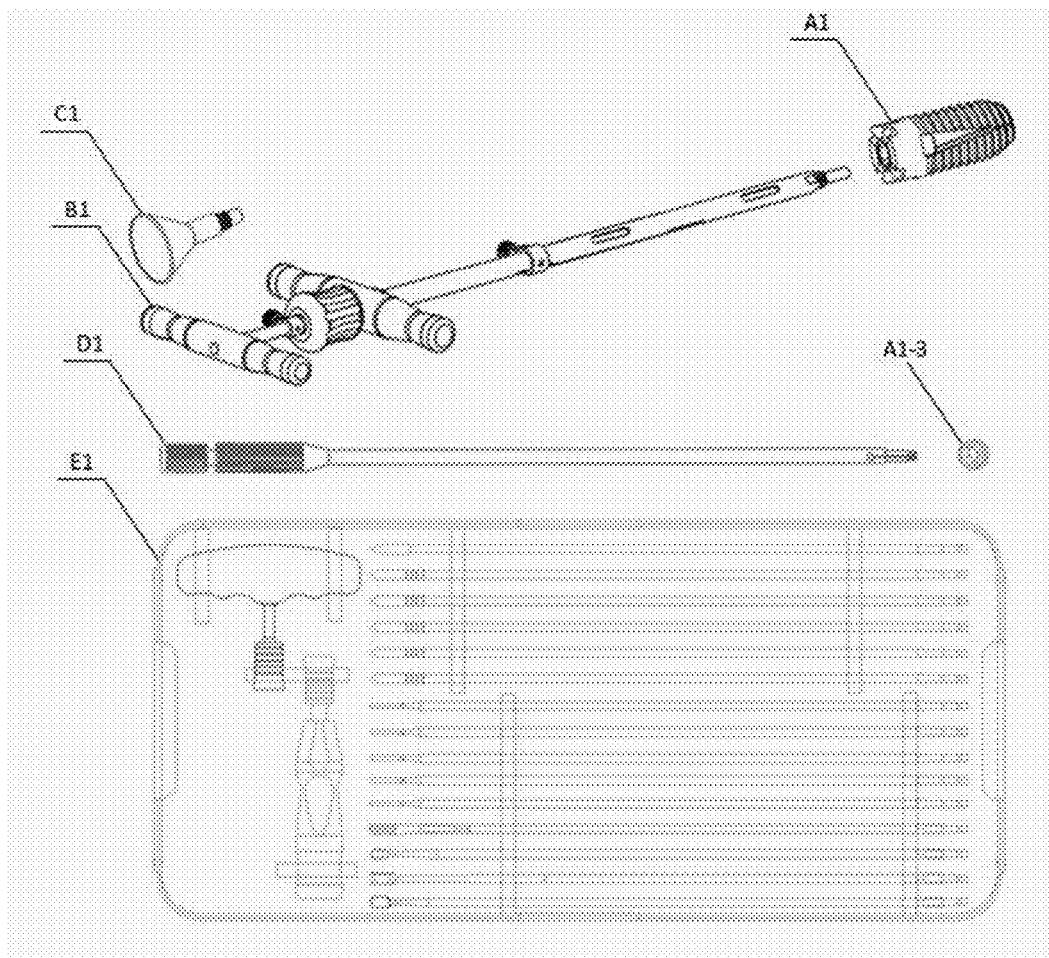
FIG. 1 is a schematic diagram of the overall structure of a surgical instrument assembly for intervertebral foramen endoscope fusion according to an embodiment of the present application.
Figure 2:
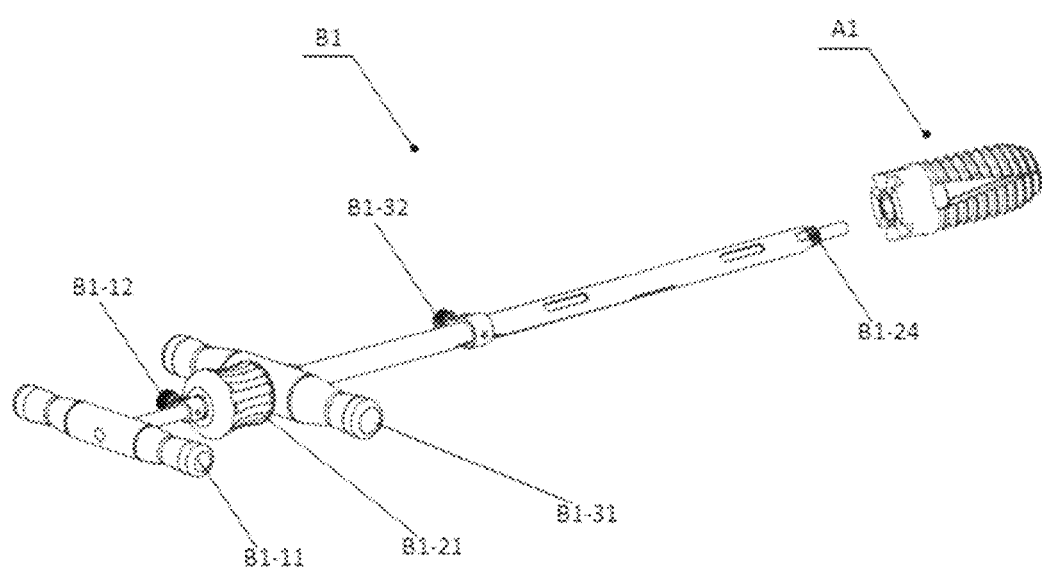
FIG. 2 is a schematic diagram of a three-dimensional structure of a holder for intervertebral foramen endoscope fusion according to an embodiment of the present application.
Figure 3:
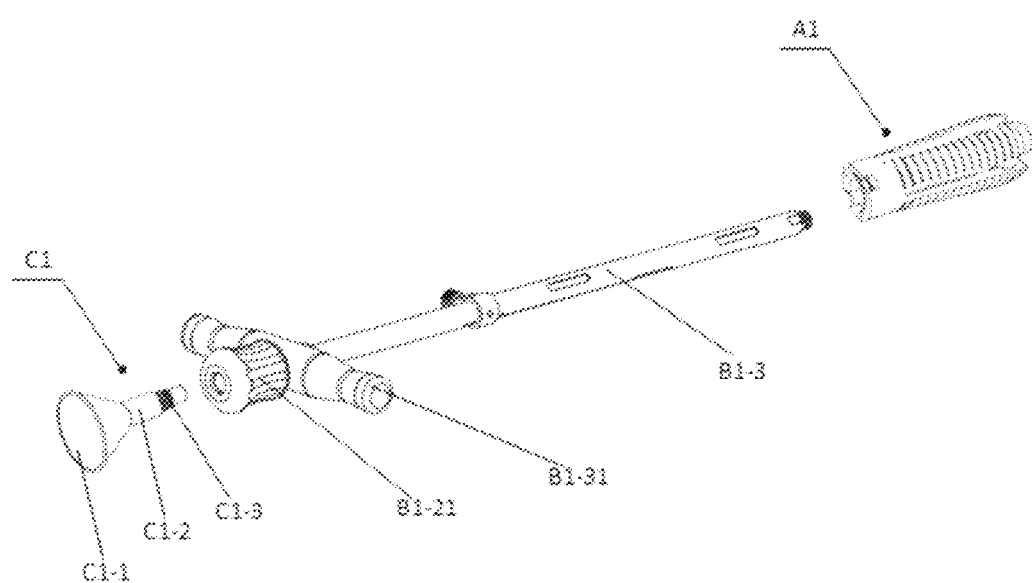
FIG. 3 is a schematic diagram showing the position relation between a fusion cage (after expansion), a holder and a bone grafting funnel for intervertebral foramen endoscope fusion according to an embodiment of the present application.
Figure 4:
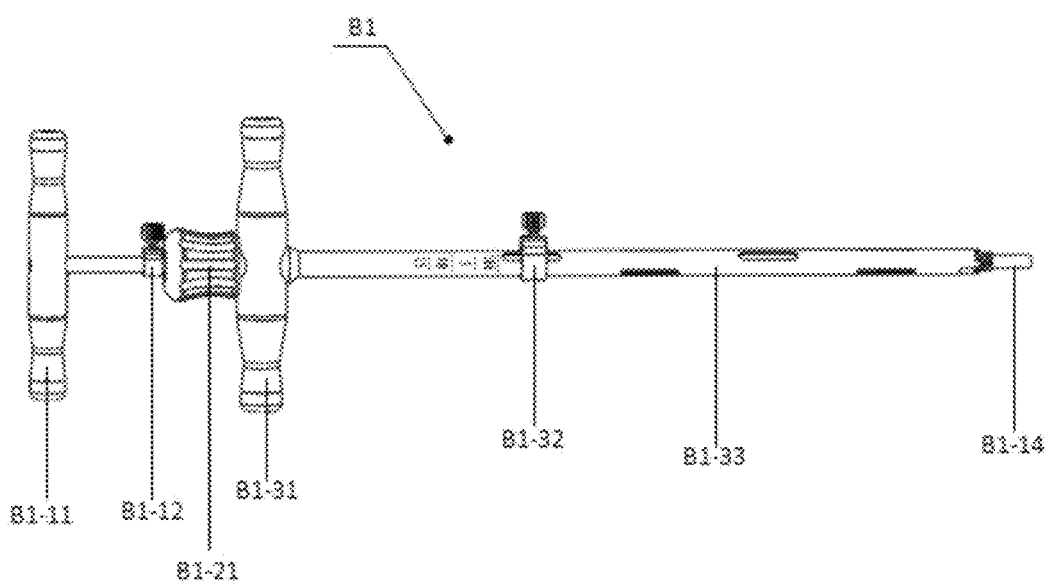
FIG. 4 is a front view of a holder for intervertebral foramen endoscope fusion according to an embodiment of the present application.
Figure 5:
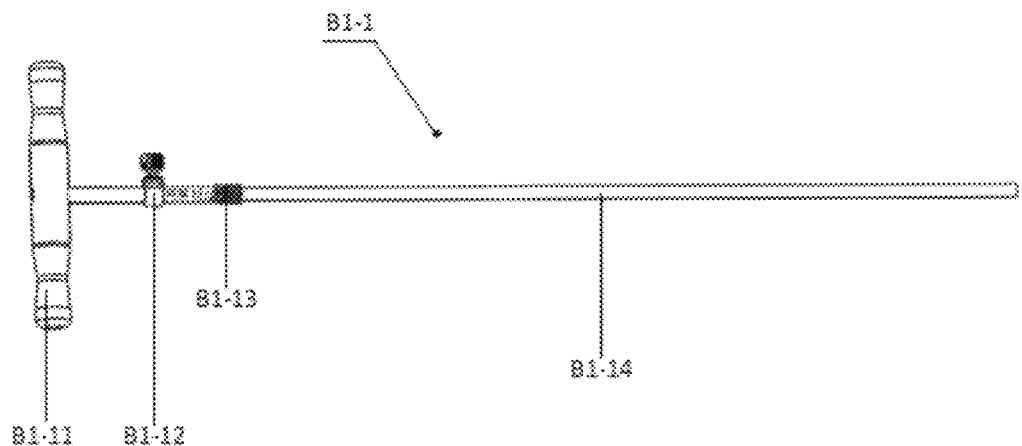
FIG. 5 is a schematic diagram of an inner rod structure according to an embodiment of the present application.
Figure 6:
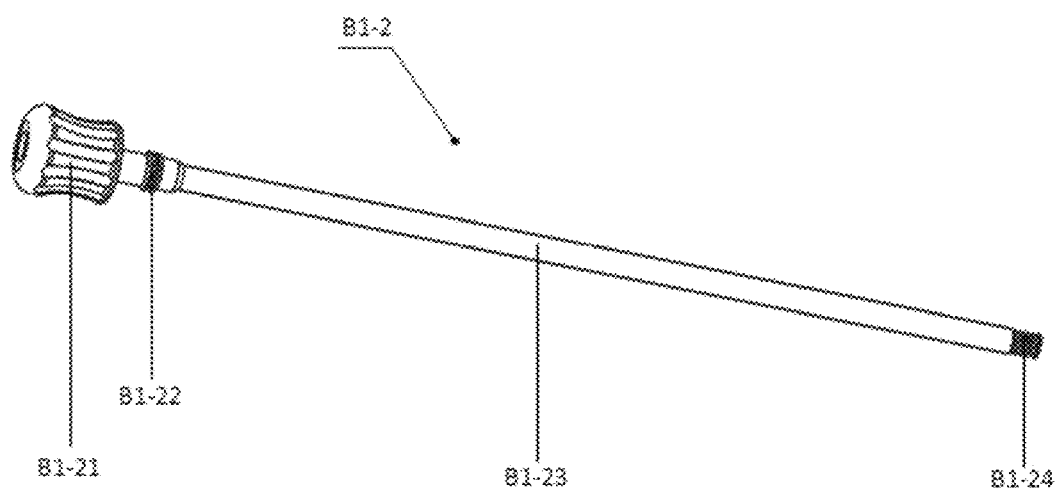
FIG. 6 is a schematic diagram of an anti-torsion sleeve structure according to an embodiment of the present application.
Figure 7:
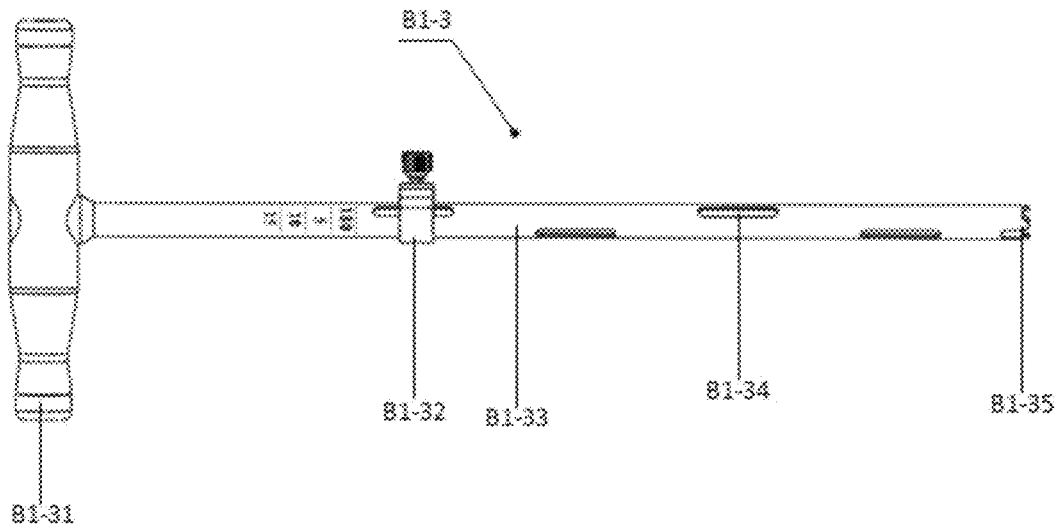
FIG. 7 is a schematic diagram of an outer sleeve structure according to an embodiment of the present application.
Figure 8:
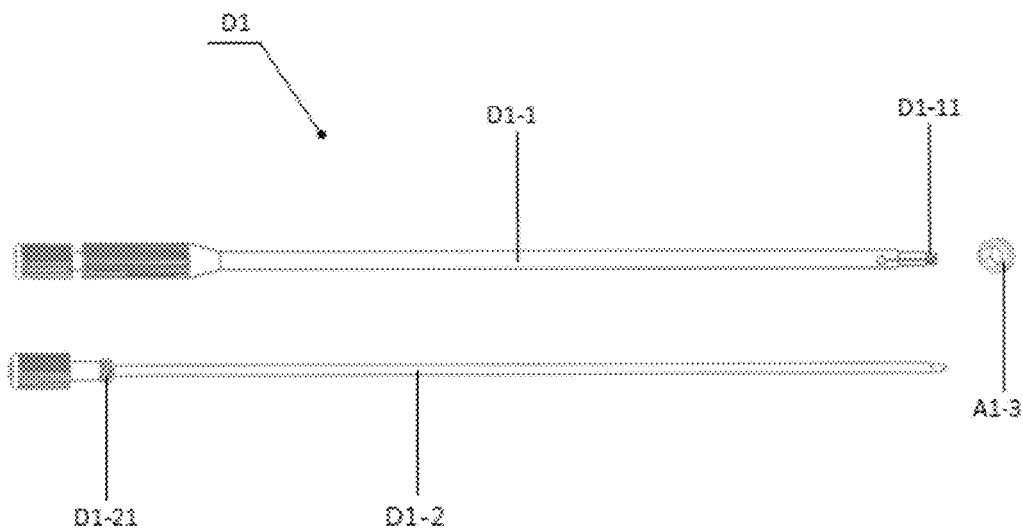
FIG. 8 is a schematic diagram of a split structure of a pre-tightening wrench according to an embodiment of the present application.
Figure 9:
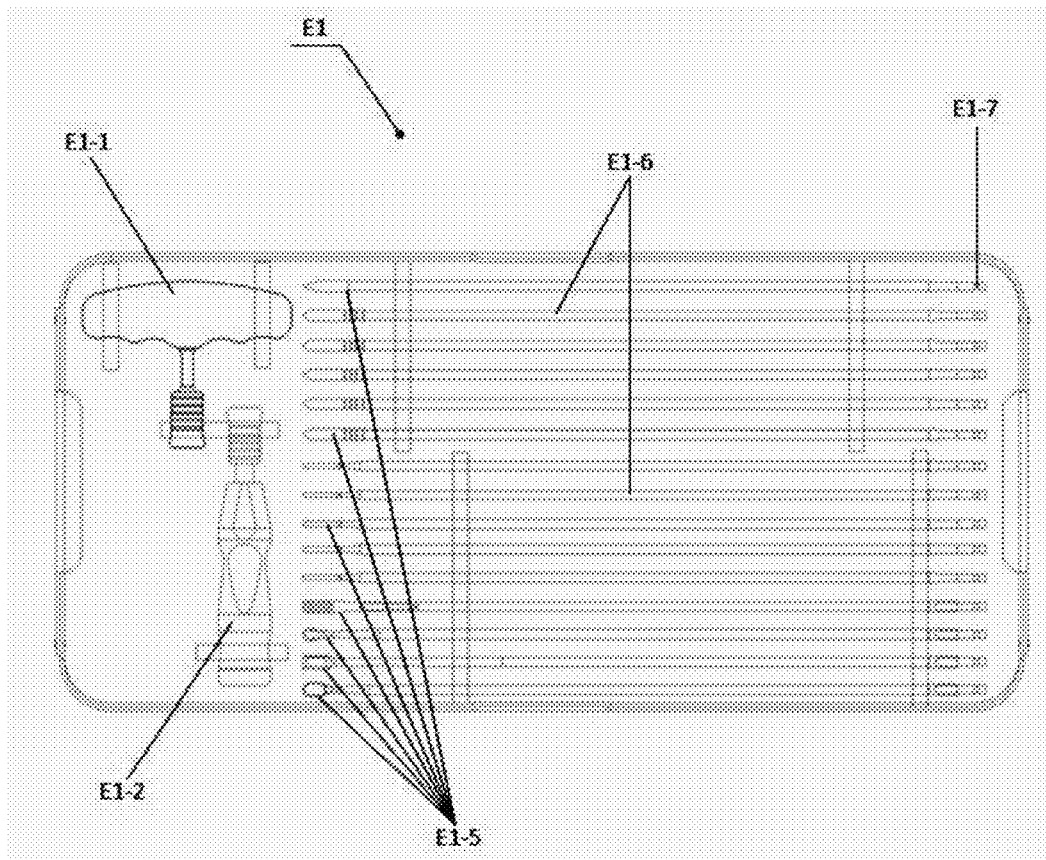
FIG. 9 is a structural schematic diagram of part of the handles and the operating heads in a surgical instrument assembly according to an embodiment of the present application.
Figure 11:
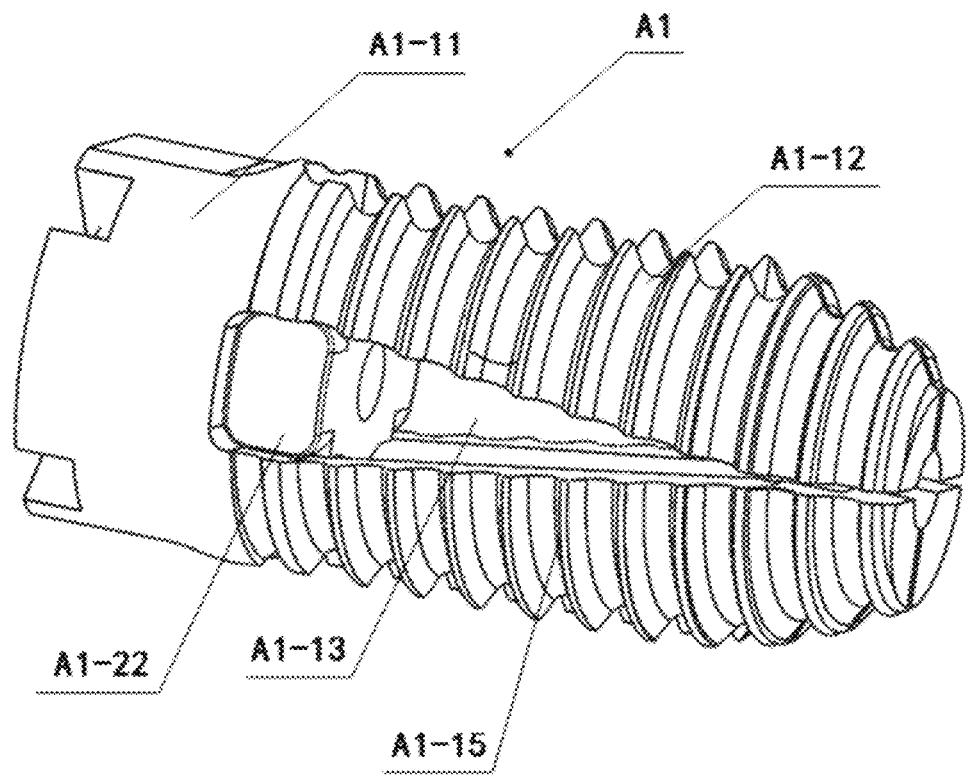
FIG. 11 is a structural schematic diagram of one side of a fusion cage for intervertebral foramen endoscope fusion according to an embodiment of the present application.
Figure 12:
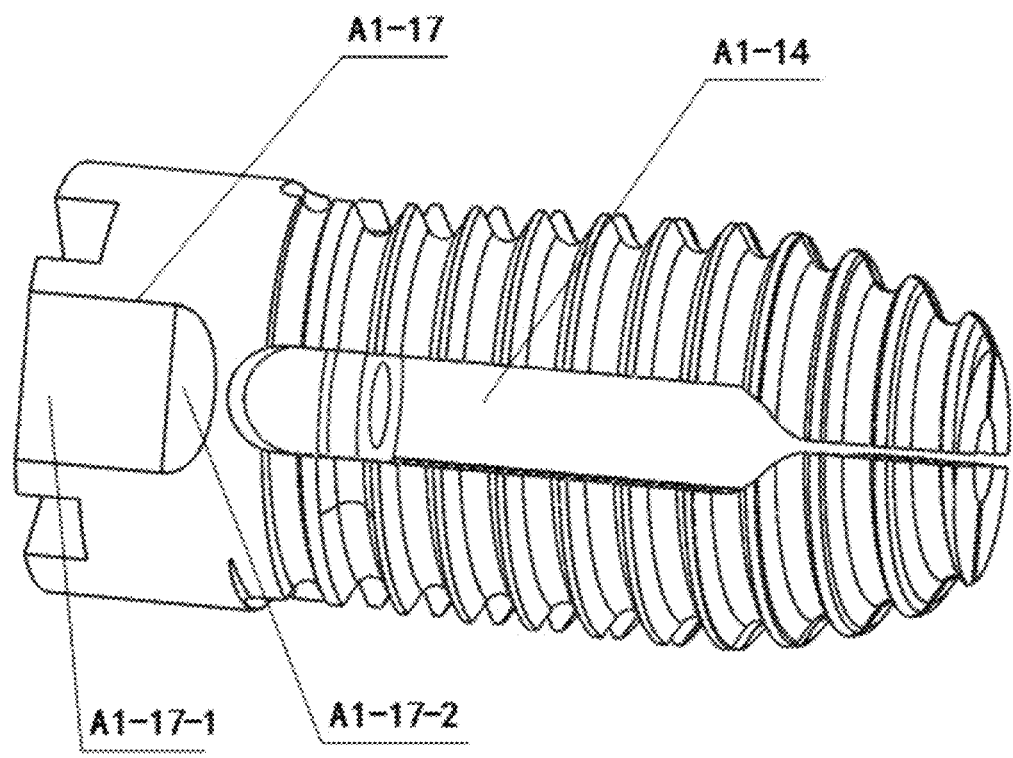
FIG. 12 is a structural schematic diagram of another side of the fusion cage according to an embodiment of the present application.
Figure 16:
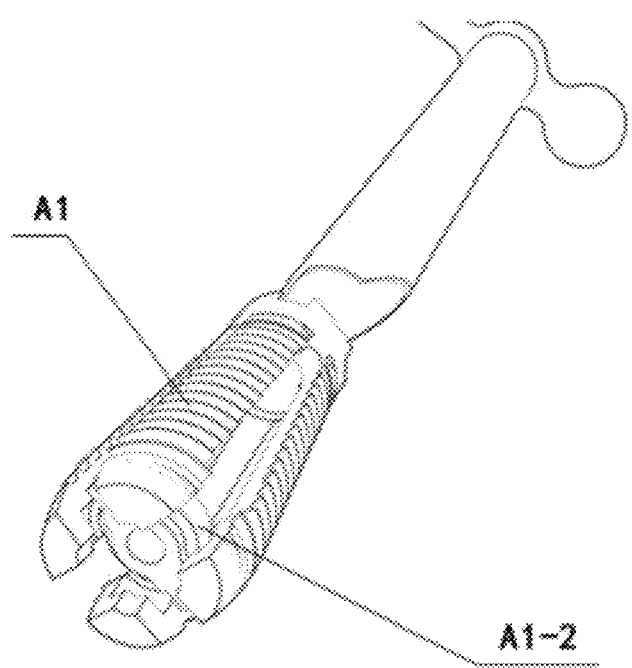
FIG. 16 is a structural schematic diagram of the fusion cage and the holder according to the embodiment of the present application in a coordinated implantation and expansion state.
Figure 17:
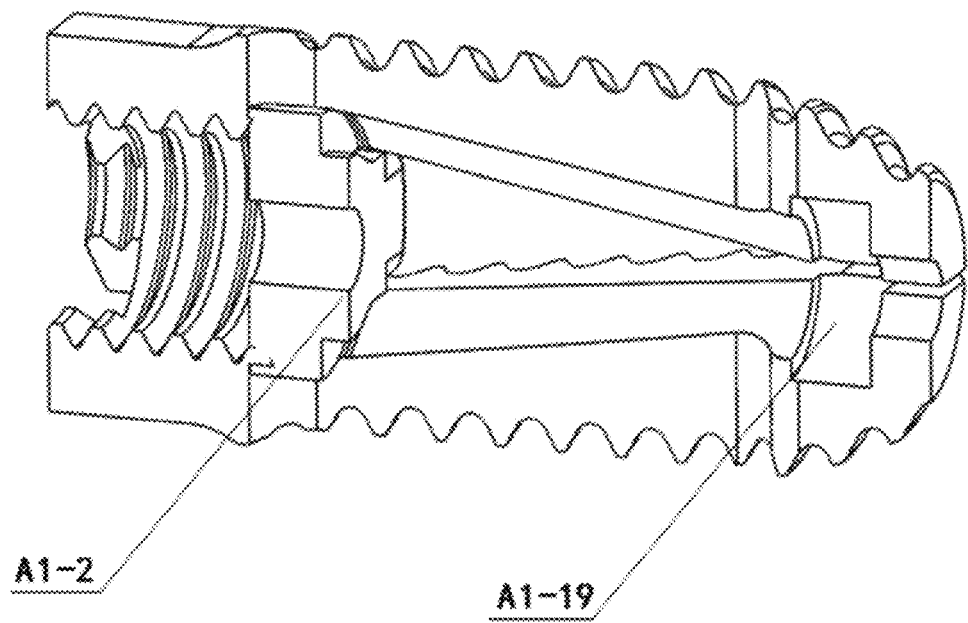
FIG. 17 is a sectional structural diagram of a fusion cage according to an embodiment of the present application.

The corresponding relationship between reference numerals and component names in FIGS. 1 to 17 is as follows:

A1. fusion cage;
A1-1. fusion cage body;
A1-11. holding body;
A1-12. expanding body;
A1-13. slideway;
A1-14. bone overflow channel;
A1-15. triangular tooth;
A1-16. breach;
A1-17. window notch;
A1-17-1. plane;
A1-17-2. slope;
A1-18. screw plug mounting hole;
A1-19. clamping groove.
A1-2. expanding part;
A1-21. central through hole;
A1-22. expanding shoulder;

A1-23. disk body;
A1-24. irregular arc block;
A1-25. arc wall;
A1-26. arched surface;
A1-27. right angle area;
A1-3. screw plug;
A1-31. thread;
A1-32. polygonal inner hole;
B1. holder;
B1-1. inner rod;
B1-11. first handle;
B1-12. first limit assembly;
B1-13. first thread section;
B1-14. straight rod;
B1-2. anti-torsion sleeve;
B1-21. knob;
B1-22. second thread section;
B1-23. casing;
B1-24. external thread section;
B1-3. outer sleeve;
B1-31. second handle;
B1-32, second limit assembly;
B1-33. sleeve;
B1-34. a strip of through hole;
B1-35. square tooth;
C1. bone grafting funnel;
C1-1. funnel cavity;
C-2. neck;
C1-3. third thread section;
D1. pre-tightening wrench;
D1-1. outer pipe;
D1-11. head of outer pipe;
D1-2. thimble;
D1-21. fourth thread section;
E1. intervertebral space treatment instrument package;
E1-1. vertical quick-release handle;
E1-2. longitudinal quick-release handle;
E1-3. clamping part;
E1-4. silicone handle;
E1-S. operating head;
E1-6. long pole;
E1-7. snap ring groove.

DETAILED DESCRIPTION OF THE EMBODIMENTS

In order to enable those skilled in the art to better understand the technical solutions of the present application, the present application is described in detail below in conjunction with surgical instrument assemblies including fusion cages and holders, drawings of each component, and embodiments.

Referring to FIG. 1 to FIG. 17, the present application provides a surgical instrument assembly for intervertebral foramen endoscope fusion, which at least includes a holder, a bone grafting funnel and a fusion cage. The surgical instrument assembly may further include pre-tightening wrenches and various surgical operation instruments that may be used in the intervertebral foramen endoscope fusion, such as bone reamers, bone files, annular scrapers, square scrapers, curettes, vertebral distractors, test molds, etc.

The fusion cage A1 for intervertebral foramen endoscope fusion in the present application includes a fusion cage body A1-1 and an expanding part A1-2. The fusion cage body A1-1 further includes a holding body A1-11 and expanding bodies A1-12. The holding body A1-11 is provided with a positioning clamp matched with the holder B1, and the clamping is described hereinafter.

The external surface of the expanding body A1-12 of the fusion cage is provided with teeth and encloses an inner cavity. The main function of the teeth is to make the fusion cage screw into the intervertebral space under the cooperation with the bolder, and closely adhere to the upper and lower endplates of the vertebral body and the implanted broken bone to achieve bony fusion. The teeth may be triangular tooth A1-15, or other forms of tooth structure. In an embodiment, the number of the expanding bodies A1-12 is at least two, each expanding body A1-12 is circumferentially arranged along one end of the holding body A1-11, and all expanding bodies A1-12 enclose an inner cavity. In this embodiment, four expanding bodies A1-12 are illustrated in the drawings. The number of expanding bodies A1-12 is not limited to the above, but may also be other numbers, such as three or five.

Bone overflow channels A1-14 are formed between at least a pan of adjacent expanding bodies A1-12 in the present application, that is, the bone overflow channels A1-14 are formed between two adjacent expanding bodies A1-12. The bone overflow channels A1-14 may extend in the longitudinal direction to the head of the expanding body A1-12. The bone overflow channels A1-14 may be evenly arranged along the circumferential direction. The bone overflow channel A1-14 is formed, in a strip of unsealed groove, between the two expanding bodies A1-12. The strip of groove structure is conducive to the uniform overflow of implanted substances and the uniform expanding of each expanding body A1-12.

This specification provides an embodiment in which four support bodies form two symmetrical bone overflow channels A1-14.

In the above embodiment, if the expanding part A1-2 is close to a first end of the holding body A1-11 the head ends of the expanding bodies A1-12 are relatively close to each other. If the expanding part A1-2 slides to the head end of the expanding body A1-12, the head end of each expanding body A1-12 is relatively opened. The support bodies are arranged independently of each other, and a relatively small force is applied to the expanding part A1-12 to increase the space between the support bodies and increase the volume of the inner cavity.

In an embodiment, a slideway A1-13 is formed between part of two adjacent expanding bodies A1-12. Taking the four support bodies as an example, the four support bodies may form two bone overflow channels A1-14 and two slideways A1-13, the bone overflow channel A1-14 and the slideway A1-13 are spaced apart from each other, and the two slideways A1-13 are also symmetrically arranged. The slideway A1-13 extends along the longitudinal direction. The closer it is to the head end of the expanding body A1-12, the narrower the slideway A1-13. The expanding part A1-2 has an expanding shoulder A1-22 which is in sliding fit with the slideway A1-13. Because the sixe of the slideway A1-13 decreases along the sliding direction, the distance between adjacent expanding bodies A1-12 increases under the action of expanding shoulders A1-22, and then the size of the inner cavity increases.

The inner cavity wall close to the head end of the expanding body A1-12 is provided with a positioning portion for positioning the expanding part A1-2 at the head end of each expanding body A1-12. The positioning portion may be a clamping groove A1-19. If the expanding part A1-2 slides to a predetermined position, a part of the expanding part A1-2 is clamped inside the clamping groove A1-19. The positioning portion may also have other structures. The expanding part A1-2 slides to the position of the positioning portion, and the diameter of the expanding body A1-12 becomes the largest.

It may be seen from the above that the fusion cage in this specification is an expandable fusion cage. When the expanding part A1-2 is located near the end of the holding body A1-11, the radial dimension of the expanding body A1-12 is relatively small, which is beneficial for the fusion cage in a smaller size to be implanted into the body along the instrument. After the fusion cage is implanted into the body, the inner rod B1-1 of the holder B1 pushes the expanding part A1-2 to the head end of the expanding body A1-12, thereby increasing the radial size of the expanding body A1-12 to playa supporting role.

The present application provides a holder B1, which is used in conjunction with the above fusion cage. The holder B1 includes an inner rod B1-1, an anti-torsion sleeve B1-2, and an outer sleeve B1-3, which may be set in the listed sequence from inside to outside. In other words, the anti-torsion sleeve B1-2 is sleeved in the outer sleeve B1-3, and the inner rod B1-1 is sleeved in the anti-torsion sleeve B1-2.

The inner rod B1-1 is used to push the expanding part inside the fusion cage. The head end of the inner rod B1-1 abuts against the expanding part A1-2 of the fusion cage, and the expanding part moves along the axial direction to change the radial size of the expanding body A1-12 of the fusion cage. That is, the inner rod B1-1 mainly functions as applying a pushing force to the expanding part A1-2, so as to push the expanding part A1-2 to slide axially to the head end of the expanding body A1-12.

The head end of the anti-torsion sleeve B1-2 is provided with an external thread section B1-24. The external thread section B1-24 matches and connects with the screw plug mounting hole A1-18 of the holding body A1-11 of the fusion cage. The screw plug mounting holes A1-18 of the holding body A1-11 are internally threaded holes used to match the screw plugs A1-3 in the cap sealing process. The tail end of the anti-torsion sleeve B1-2 is further provided with a matching structure for matching with the bone grafting funnel C1. In an embodiment, the matching structure of the anti-torsion sleeve B1-2 may be a threaded structure, or any other structure.

The head end of the outer sleeve B1-3 is matched with the holding body A1-11 of the fusion cage A1 to restrict the fusion cage from rotating along its axis. In an embodiment, the outer end surface of the holding body A1-11 may be provided with a fit to restrict the circumferential rotation of the fusion cage and the outer sleeve. This specification illustrates at least two breaches A1-16 on the holding body A1-11, and each breach A1-16 is arranged in the circumferential direction. The end of the outer sleeve B1-3 of the holder B1 is provided with a toothed end inserted into the breach A1-16. The number of breaches A1-16 may be three or four or six, and so on. The head end of the outer sleeve B1-3 is provided with square tooth B1-35.

In the assembled holder B1, both ends of the inner rod B1-1 are located outside the anti-torsion sleeve B1-2, and both ends of the anti-torsion sleeve B1-2 are located outside the outer sleeve B1-3, which is convenient for operation. The lengths of the inner rod B1-1, the anti-torsion sleeve B1-2 and the outer sleeve B1-3 may be reasonably set according to the specific application environment.

During the operation, the anti-torsion sleeve B1-2 and the outer sleeve B1-3 of the holder B1 are combined outside the body, then the anti-torsion sleeve B1-2 is threadedly connected with the screw plug mounting hole A1-18 of the fusion cage, and the outer sleeve B1-3 and the holder are circumferentially limited and matched to realize the clamping of the fusion cage. Then an assembly formed by combing the holder B1 and the fusion cage A1 is delivered into the body, and the inner rod B1-1 is inserted into the anti-torsion sleeve B1-2, so that the head end of the inner rod pushes the expanding part A1-2 to move to the head end of the support body axially to increase the radial size of the support body. After the expanding part A1-2 moves to the predetermined position, the inner rod B1-1 may be taken out from the anti-torsion sleeve B1-2, and then the bone grafting funnel is mounted on the tail end matching structure of the anti-torsion sleeve B1-2 for bone grafting operation. After bone grafting is completed, the anti-torsion sleeve B1-2 is screwed out of the fusion cage and taken out of the body, and the end of the pre-tightening wrench D1 fixed with the screw plug A1-3 extends from the inner cavity of the outer sleeve B1-3 and is mounted in the screw plug mounting hole A1-18 of the fusion cage to complete the cap sealing operation. Finally, the outer sleeve B1-3 is separated from the fusion cage A1 and taken out of the body.

It may be seen from the above description that the holder B1 provided by the present application may realize the functions of holding, implanting, expanding, bone grafting, cap sealing, etc., which may greatly reduce the operation workload of doctors and realize efficient and high-quality operation.

Specifically, the inner rod B1-1 may include a straight rod B1-14 and a first handle B1-11 connected to the tail end of the straight rod B1-14. The straight rod B1-14 is sleeved in the anti-torsion sleeve B1-2, and the straight rod B1-14 includes a first thread section B1-13 for threaded connection with the anti-torsion sleeve B1-2. Correspondingly, the anti-torsion sleeve B1-2 is provided with an internal thread section that cooperates with the first thread section B1-13. The first handle B1-11 is located outside the anti-torsion sleeve B1-2. When the fusion cage A1 is expanded, the head end of the straight rod B1-14 must also extend out of the head end of the anti-torsion sleeve B1-2.

In the above embodiment, the inner rod B1-1 is connected with the anti-torsion sleeve B1-2 through threads to realize axial reciprocating motion, which may control the stability, controllability of the axial movement of the inner rod B1-1, achieving high displacement dimensional accuracy.

The straight rod B1-14 includes a first scale rod section. The first scale rod section is close to a side of the first handle B1-11 and exposed outside the anti-torsion sleeve B1-2. The first scale rod section is provided with scale values for marking the depth of the straight rod B1-14 entering the anti-torsion sleeve B1-2. The holder B1 further includes a first limit assembly B1-12. The first limit assembly B1-12 is slidable or lockable relative to the first scale rod section, and configured to limit the axial position of the straight rod B1-14. Once the movement displacement of the straight rod B1-14 is determined, the first limit assembly B1-12 is fixed on the corresponding scale of the first scale rod section, the straight rod B1-14 is rotated to the scale, and the first limit assembly B1-12 may limit the further rotation of the straight rod B1-14. In this way, the movement displacement of the straight rod B1-14 may be further accurately controlled, which is beneficial to improving the accuracy of the operation.

In the above embodiments, along the axial direction, the anti-torsion sleeve B1-2 includes a large-diameter hollow knob B1-21 and a small-diameter casing B1-23 that are coaxially arranged. The knob B1-21 has a thread section for threaded fitting with the first thread section B1-13 of the straight rod and for fitting with the bone grafting funnel C1. Correspondingly, the bone grafting funnel C1 may include a funnel cavity C1-1 and a neck C1-2 that are integrally connected with each other, a third thread section C1-3 is arranged at the end of the neck C1-2 away from the funnel cavity C1-1, and the third thread section C1-3 may be matched with the thread section of the knob B1-21, so that the bone grafting funnel C1 may be assembled on the anti-torsion sleeve B1-2 to provide instrument support for doctors to bone graft. In addition, the design of quickly mounting the bone grafting funnel C1 on the holder B1 greatly reduces the operation risk and improves the operation efficiency. The head end of the casing B1-23 is provided with an external thread section B1-24 for mating connection with the screw plug mounting hole A1-18 of the holding body A1-11 of the fusion cage A1.

In deed, to achieve precise mounting of the fusion cage, the outer sleeve B1-3 may include a sleeve B1-33 and a second handle B1-31 mounted on the sleeve B1-33. The casing B1-23 of the anti-torsion sleeve B1-2 is sleeved in the sleeve B1-33, and the knob is outside the sleeve B1-33. The sleeve B1-33 includes a second scale rod section, which is configured to mark the depth of the sleeve B1-33 into the intervertebral space.

The outer sleeve B1-3 may further include a second limit assembly B1-32, which is slidable or lockable relative to the second scale rod section. The function of the second limit assembly B1-32 is the same as the function of the first limit assembly B1-12, and is not repeated here.

In the above embodiment, the peripheral surface of the sleeve B1-33 may also be provided with multiple strips of through holes B1-34, and the arrangement of the strips of through holes B1-34 is convenient for cleaning and disinfecting the instrument.

The second handle B1-31 and the anti-torsion sleeve B1-2 may also be threadedly connected with each other, that is, the anti-torsion sleeve B1-2 is provided with a second thread section B1-22, the second handle B1-31 is provided with internal threads, and the second thread section B1-22 of the anti-torsion sleeve passes through the through hole on the second handle and extends into the sleeve B1-33.

The specific structure of the expanding part A1-2 is described below.

In an embodiment, the expanding part A1-2 includes a disk body A1-23 having a central through hole A1-21, the peripheral wall of the disk body A1-23 includes two arc walls A1-25 and two platforms, the arc walls A1-25 are spaced apart from the platforms, and the platforms may be formed by cutting sector blocks on the cylindrical outer surface. Two expanding shoulders A1-22 extend radially from the two platforms respectively, the expanding shoulders A1-22 extend into the slideway A1-13, and the arc walls A1-25 are abutted and matched with the corresponding positions of the inner cavity wall, so that the arc walls A1-25 may stably support the inner cavity wall if the fusion cage is in an expanding state.

In deed, the four corners of the expanding shoulder A1-22 may be gently chamfered.

Further, the width of the expanding shoulder A1-22 is smaller than the width of the platform, so that a right angle area A1-27 is formed between the side wall of the expanding shoulder A1-22 and its adjacent arc wall A1-25. The right angle area A1-27 cooperates with the side wall of the corresponding expanding body A1-12 forming the slideway A1-13 to restrict the circumferential rotation of the expanding part A1-2. In this way, the expanding shoulder A1-22 may only slide in the axial direction and may not move in the circumferential direction, so that the movement controllability of the expanding part A1-2 is relatively high.

Furthermore, the end face of the disc body A1-23 facing the holding body is a plane, and the end face of the disc body A1-23 facing the head end is further provided with an irregular arc block A1-24. The irregular arc block A1-24 is provided with a through hole coaxial with the central through hole. The irregular arc block A1-24 includes at least a section of arched surface A1-26 coaxial with the arc wall A1-25. In the case that the arc wall A1-25 is matched with the clamping groove A1-19 for limiting, the arc wall A1-25 is limited with the clamping groove, and the arched surface A1-26 supports the inner cavity wall at the front end of the clamping groove A1-19.

The arched surface A1-26 further supports the inner cavity wall at the front end of the clamping groove A1-19, and increases the mounting stability of the fusion cage.

In the above embodiments, in the case that the expanding part A1-2 is located at the head end of expanding body A1-12, the peripheral dimension of the whole structure formed by individual expanding bodies A1-12 gradually increases from the holding body A1-11 to the head end of expanding body A1-12. This structure conforms to the physiological curvature of the human body with a large front side and a small rear side of the lumbar intervertebral space.

The material of the fusion cage in the present application may be a titanium alloy material with strong support and permanence, and the metal characteristics of the titanium alloy may not interfere with the nuclear magnetic resonance examination.

In the present application, the screw plug mounting hole A1-18 of the holding body A1-11 is not only matched with the screw plug A1-3, but also may be matched with the head end external thread section B1-24 of the anti-torsion sleeve B1-2 of the holder B1. Correspondingly, the screw plug A1-3 is of a cylindrical shape with threads A1-31 on the curved surface of the cylinder, with a polygonal groove adapted to the pre-tightening wrench at one end, and with a flat plane on the other end. And the screw plug A1-3 is matched and assembled with the internal thread of the screw plug mounting hole of the holding body A1-11, thereby realizing the sealing and fixing of the fusion cage. In addition, the screw plug A1-3 may also be used as the cap of the fusion cage to use bone morphogenetic protein (that is, osteogenic protein) to accelerate the bone fusion of the affected area.

As mentioned above, the screw plug A1-3 has a polygonal groove, the cross section of the screw plug A1-3 is a polygonal inner hole A1-32, which is used for cooperating with the pre-tightening wrench D1.

In order to allow the doctor to quickly judge the position of the fusion cage mounted on the human body, the following settings are further made in this specification.

The outer peripheral wall of the holding body A1-11 is further provided with a window notch A1-17. The window notch A1-17 includes a plane and a slope A1-17-2 abutting the plane A1-17-1 along the axial direction. One end of the plane A1-17-1 extends to the outer end surface of the holding body A1-11, and the other end abuts the slope A1-17-2. The height of the slope A1-17-2 gradually rises from the plane to the expanding body A1-12.

When the holder B1 and the fusion cage A1 are assembled outside the human body, the second handle B1-31 may be arranged in parallel with the window notch A1-17. The holder B1 holding the fusion cage rotates into the intervertebral space, and the doctor may determine the position of the fusion cage A1 according to the state of the second handle B1-31, so that the two window notches A1-17 arranged on the symmetry plane respectively correspond to the upper endplate and the lower endplate between intervertebral spaces.

The pre-tightening wrench D1 of the surgical instrument assembly for intervertebral foramen endoscope fusion of the present application includes a hollow outer pipe D1-1 and a thimble D1-2 arranged in the inner cavity of the outer pipe D1-1. The thimble D1-2 may move axially relative to the hollow outer pipe, and the thimble D1-2 has a conical head. The shape of the head of outer pipe D1-I1 is matched with the polygonal inner hole A1-32 of the screw plug A1-3, and the head of the outer pipe D1-1 is circumferentially unsealed. If the conical head of thimble D1-2 is mounted on the head of the outer pipe, the head of outer pipe may be expanded to increase the outer diameter, and then fixed in polygonal inner hole A1-32 of the screw plug A1-3. If the screw plug A1-3 is mounted inside the fusion cage, the thimble D1-2 moves outward to realize the reduction in the size of the head of the outer pipe, loosen the screw plug A1-3, and move the pre-tightening wrench D1 out of the human body.

In the above embodiment, the hollow outer pipe D1-1 and the thimble D1-2 are connected by screw threads in an axial moving manner. That is, a fourth thread section D1-21 is arranged outside the thimble D1-2 near the outer end of the thimble D1-2, and the fourth thread section D1-21 may be matched with the built-in thread of the outer pipe D1-1.

In order to facilitate the operation, both the thimble D1-2 and the outer pipe D1-1 may be provided with a handle. In the above embodiments, the surgical instrument assembly further includes multiple surgical operation instruments for intervertebral foramen endoscope fusion. The above-mentioned surgical operation instruments may be stored in the intervertebral space treatment instrument package E1. Each surgical operation instrument includes a long pole E1-6 with an operating head E1-5 at one end and at least one handle detachably connected to the other end of the long pole E1-6, and the diameter of the long pole E1-6 is smaller than the entrance sine of the head end of the intervertebral foramen endoscope. The main forms of operating head E1-5 include: bone reamer, bone file, annular scraper, square scraper, curette, vertebral spreader, and test mould, which are mainly tools used in intervertebral foramen endoscope fusion.

The tail side of the long pole E1-6 may be inserted upside down into the inner cavity of the intervertebral foramen endoscope instrument channel through the head end of the intervertebral foramen endoscope instrument channel, and the tail side of the long pole E1-6 protrudes from the tail end of the intervertebral foramen endoscope instrument channel, and then the operating head E1-5 is mounted at the corresponding end of the long pole E1-6. The instrument approaches into the instrument operation channel from the intervertebral foramen endoscope lens end approach, so as to realize the large-area design of each instrument operating head E1-5. The visualized instrument support also improves the efficiency of surgical treatment of the patient's intervertebral space.

This specification shows a specific embodiment in which the first handle B1-11 and the second handle B1-31 are both vertical, i.e., a T-shape shows between the outer sleeve and the first handle B1-11 as well as the second handle B1-31, so that the handle torque is relatively large, and it is labor-saving in use.

In practice, the first handle B1-11, the second handle B1-31, and other handles herein may be in other shapes.

For example, the above-mentioned handles cooperable with corresponding instruments may include vertical quick-release handles E1-1 and longitudinal quick-release handles E1-2. Each of the vertical quick-release handle E1-1 and the longitudinal quick-release handle E1-2 include a silicone handle E1-4 and a clamping part E1-3. And the silicone handles E1-4 of the vertical quick-release handle E1-1 and the longitudinal quick-release handle E1-2 are respectively connected with their respective clamping parts E1-3 in an integrated T-shaped connection and I-shaped connection. Doctors may choose different shapes of handles according to their own surgical habits and the surgical operation track of matching instruments (such as bone files, circular scrapers, square scrapers, curettes, etc., which are more suitable for vertical handles).

The clamping part E1-3 mainly include a spring, a clamping bead and a square inner cavity, and the square inner cavity may be matched with the square tail end of the long pole E1-6 to prevent the long pole E1-6 from making circumferential movement during operation. The long pole E1-6 is fixed in the clamping part E1-3 by the snap ring groove E1-7 of the long pole E1-6, and the built-in spring may control the long pole E1-6 to assemble or detach from the clamping part E1-3.

It should be noted that the orientation or positional relationships indicated by terms such as "horizontal", "inner", "outer", and the like are based on the orientation or positional relationships shown in the drawings, and are merely for the convenience of describing the present application and the simplification of the description, and do not indicate or imply that the device or element referred to must have a particular orientation, or be configured and operated in a particular orientation, and therefore should not be construed as a limitation to the scope of the present application. In addition, the terms "first", "second" and the like are for purpose of description, and should not be construed as indicating or implying relative importance.

In a description of the present application, it should be noted that, unless otherwise explicitly specified and defined, term "connection" should be understood in a broad sense, for example, the term may imply a fixed connection, a detachable connection, or an integral connection; a direct connection or an indirect connection through intermediary. For those skilled in the art, the specific meaning of the above terms in the present application may be understood in the light of specific circumstances.

The holder and surgical instrument assembly for intervertebral foramen endoscope fusion according to the present application are described in detail hereinbefore. The principle and the embodiments of the present application are illustrated herein by specific examples. The above description of examples is only intended to help the understanding of the method and spirit of the present application. It should be pointed out that, various improvements and modifications can be made by those skilled in the art without departing from the principle of the present disclosure, and these all fall within the protection scope of the present application.

The invention claimed is:

1. A holder for intervertebral foramen endoscope fusion, comprising an inner rod, an anti-torsion sleeve and an outer sleeve which are sleeved from inside to outside and are movable relatively along an axial direction; wherein the inner rod is configured for pushing the an expanding part inside a fusion cage;

a head end of the anti-torsion sleeve is provided with an external thread section, the external thread section is configured for matching and connecting with a screw plug mounting hole of a holding body of the fusion cage, and a tail end of the anti-torsion sleeve is provided with a matching structure for matching with a bone grafting funnel;

a head end of the outer sleeve is matched with the holding body of the fusion cage to restrict the rotation of the fusion cage along an axis of the fusion cage;

the inner rod comprises a straight rod and a first handle connected to a tail end of the straight rod. wherein the straight rod is sleeved in the anti-torsion sleeve and the straight rod comprises a first thread section for threaded connection with the anti-torsion sleeve, and the first handle is located outside the anti-torsion sleeve; and the straight rod comprises a first scale rod section, wherein the first scale rod section is close to a side of the first handle and exposed outside the anti-torsion sleeve the first scale rod section is provided with scale values for marking a depth of the straight rod entering the anti-torsion sleeve, and the holder further comprises a first limit assembly, which is slidable or lockable relative to the first scale rod section, and configured to limit an axial position of the straight rod.

2. The holder according to claim 1, wherein along the axial direction, the anti-torsion sleeve comprises a large-diameter hollow knob and a small-diameter casing that are coaxially arranged, the knob has a thread section for threaded fitting with the first thread section of the straight rod and for fitting with the bone grafting funnel, and the external thread section is arranged at a head end of the casing.

3. The holder according to claim 2,
wherein the outer sleeve comprises a sleeve and a second handle mounted on the sleeve, the casing is sleeved in the sleeve, and the knob is located outside the sleeve;
wherein the sleeve further comprises a second scale rod section, which is configured to mark a depth of the sleeve into the intervertebral space;
wherein the holder further comprises a second limit assembly, which is slidable or lockable relative to the first scale rod section, and configured to limit an axial position of the sleeve.

4. The holder according to claim 3, wherein a peripheral surface of the sleeve is provided with a plurality of strips of through holes.

5. A surgical instrument assembly for intervertebral foramen endoscope fusion, comprising:
the holder for intervertebral foramen endoscope fusion according to claim 1; and
a fusion cage and a bone grafting funnel,
wherein the fusion cage comprises a fusion cage body and an expanding part, wherein the fusion cage body comprises a holding body and expanding bodies, the number of the expanding bodies is at least two, and the expanding bodies are circumferentially arranged along one end of the holding body;
wherein the expanding bodies encloses an inner cavity, and a bone overflow channel is formed between at least part of adjacent ones of the expanding bodies;
wherein the holding body is provided with a screw plug mounting hole communicated with the inner cavity, and the screw plug mounting hole is threadedly matched with an external thread section arranged at the head end of the anti-torsion sleeve;
wherein the expanding part is slidably arranged in the inner cavity, and a slideway is formed between two adjacent ones of part of the expanding bodies, the slideway extends in a longitudinal direction, and the closer to ana head end of the expanding body, the narrower the slideway, and the expanding part has an expanding shoulder that is slidingly matched with the slideway; and wherein a clamping groove is provided at a head end of a wall of the inner cavity, and the expanding part is clamped in the clamping groove in the case that the expanding shoulder slides to the head end of the expanding body.

6. The surgical instrument assembly according to claim 5, wherein the expanding part comprises a disk body having a central through hole, a peripheral wall of the disk body comprises two arc walls and two platforms, the arc walls are spaced apart from the platforms, the two expanding shoulders extend radially from the two platforms respectively, the expanding shoulders extend into the slideway, and the arc walls are abutted and matched with corresponding positions of the wall of the inner cavity;

wherein the arc walls positioned between the two platforms is matched and clamped in the clamping groove;

wherein an end face of the disc body facing the holding body is a plane, and the end face of the disc body facing the head end is provided with an irregular arc block, the irregular arc block is provided with a through hole coaxial with the central through hole, the irregular arc block comprises at least a section of arched surface coaxial with the arc wall, and the arched surface supports the wall of the inner cavity at the front end of the clamping groove in the case that when the arc walls are matched with the clamping groove of the wall of the inner cavity for limiting.

7. The surgical instrument assembly according to claim 5, further comprising a pre-tightening wrench, which comprises a hollow outer pipe and a thimble placed in an inner cavity of the hollow outer pipe, and the outer pipe and the thimble are connected with each other by screw threads in an axial moving manner;

wherein the thimble has a conical head, a shape of a head of outer pipe is matched with a polygonal inner hole of the screw plug, and the head of the outer pipe is circumferentially unsealed; and wherein in the case that the conical head of the thimble is mounted on the head of the outer pipe, the head of the outer pipe head may is expanded to increase the outer diameter, and both the thimble and the hollow outer pipe are provided with handles.

8. The surgical instrument assembly according to claim 5, wherein the bone grafting funnel includes a funnel cavity and a neck that are integrally connected with each other, a third thread section is arranged at a far end of the neck away from the funnel cavity, the matching structure of the-a tail end of the anti-torsion sleeve is a thread, and the third thread section is connectable with the thread of the anti-torsion sleeve.

9. The surgical instrument assembly according to claim 5, further comprising a plurality of surgical operation instruments for intervertebral foramen endoscope fusion, wherein each of the surgical operation instruments comprises a long pole with an operating head at one end and at least one handle detachably connected to the other end of the long pole, a diameter of the long pole is smaller than an entrance size of the head end of the intervertebral foramen endoscope, and a tail side of the long pole is insertable upside down into the inner cavity of the intervertebral foramen endoscope instrument channel through the head end of the intervertebral foramen endoscope instrument channel, the tail side of the long pole is extended from a tail end of the intervertebral foramen endoscope instrument channel and connected to the handle.

\* \* \* \* \*